United States Patent [19]

Umezawa et al.

[11] Patent Number: 4,565,861
[45] Date of Patent: * Jan. 21, 1986

[54] SERIRUBICUM

[75] Inventors: Hamao Umezawa; Tomio Takeuchi; Masa Hamada; Hiroshi Naganawa, all of Tokyo; Tsutomu Sawa, Ayase; Takeshi Uchida, Yokohama; Masaya Imoto, Urawa, all of Japan

[73] Assignee: Microbial Chemistry Research Foundation, Tokyo, Japan

[ * ] Notice: The portion of the term of this patent subsequent to Oct. 29, 2002 has been disclaimed.

[21] Appl. No.: 567,792

[22] Filed: Jan. 3, 1984

[30] Foreign Application Priority Data

Feb. 8, 1983 [JP] Japan ................................. 58-19341

[51] Int. Cl.⁴ ............................................ C07H 15/24
[52] U.S. Cl. ..................................................... 536/6.4
[58] Field of Search ......................... 536/6.4; 424/180; 514/27

[56] References Cited

U.S. PATENT DOCUMENTS 4,316,011 2/1982 Oki et al. ............................. 536/6.4

OTHER PUBLICATIONS

Johnson et al., Cancer Treatment Reviews, (1975) 2, pp. 1-31.

Primary Examiner—Johnnie R. Brown
Assistant Examiner—Elli Peselev
Attorney, Agent, or Firm—Ladas & Parry

[57] ABSTRACT

An anthracycline, serirubicin, of the formula:

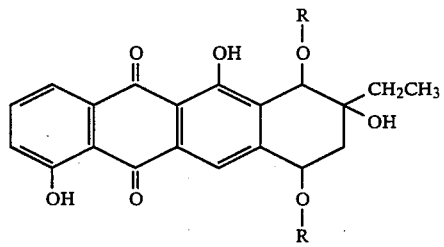

wherein R represents the substituent:

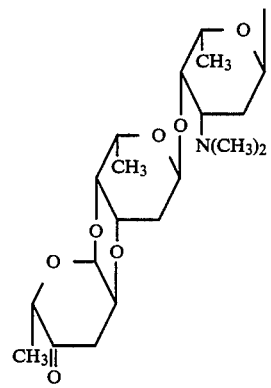

is produced by a process which comprises cultivating a strain of Streptomyces in a suitable culture medium under aerobic conditions, said strain having the ability to produce the anthracycline compound, serirubicin, and then recovering the anthracycline compound, serirubicin, from the cultured medium. This serirubicin, or an acid addition salt of the serirubicin, can be contained as the active ingredient in anti-tumor agents and in pharmaceutical compositions for treatment of infections induced by gram-positive microorganisms, whereby good results are attainable.

1 Claim, 5 Drawing Figures

SERIRUBICUM

BACKGROUND OF THE INVENTION

This invention relates to a novel anthracycline compound, processes for the production thereof, and uses thereof. Anthracycline compounds assume an important position in medicine as antibiotics for the control of cancers, and various anthracycline compounds have been proposed so far. Generally, the physiological activities of chemicals depend greatly on their chemical structures. There has been constant demand, therefore, for anthracycline compounds which differ from conventional ones in terms of the aglycone moiety, saccharide moiety, and substituent.

SUMMARY OF THE INVENTION

This invention meets the above-mentioned demand. This invention provides an anthracycline compound, referred to as serirubicin, of the formula (1) described below, and acid addition salts of the serirubicin.

This invention also provides a process for producing the anthracycline compound, serirubicin, which process comprises aerobically cultivating a serirubicin-producing strain of Streptomyces in a suitable culture medium, and recovering serirubicin from the cultured broth.

This invention further provides antitumor agents which comprise the anthracycline compound, serirubicin, of the formula (1), or its acid addition salts as the active ingredient and carriers.

This invention, moreover, provides pharmaceutical compositions for treating infections associated with gram-positive bacteria, which compositions comprise as the active ingredient the anthracycline compound, serirubicin, of the formula (1), or its acid addition salts and carriers.

This invention still provides a method of treating tumors in animals, the method comprising administering to an animal in need of such treatment a safe and effective amount of an anthracycline compound, serirubicin, of the formula (1), or an acid addition salt thereof.

The invention still further provides a method of treating gram-positive bacterial infections in animals, the method comprising administering to an animal in need of such treatment a safe and effective amount of an anthracycline compound, serirubicin, of the formula (1), or an acid addition thereof.

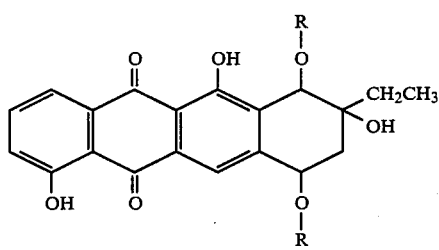

(1)

wherein R represents the substituent:

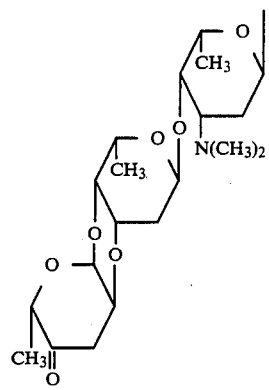

BRIEF DESCRIPTION OF THE DRAWINGS

In the drawings

In FIGS. 2 and 3, curve 1 shows the spectrum obtained in methanol; curve 2 shows the spectrum obtained in 0.1N HCl-90% methanol; and curve 3 shows the spectrum obtained in 0.1N NaOH-90% methanol.

DETAILED DESCRIPTION OF THE INVENTION

1. Details of anthracycline compound, serirubicin (1) Type and chemical structure The anthracycline compound, serirubicin, according to this invention has a chemical structure as expressed by the formula (1).

Since serirubicin has a dimethylamino group in its saccharide moiety, it can form acid addition salts. Acids to form salts upon addition reaction with serirubicin include hydrohalogenic acids (such as hydrochloric acid), sulfuric acid, and tartaric acid.

(2) Determination of chemical structure

Figure 1:
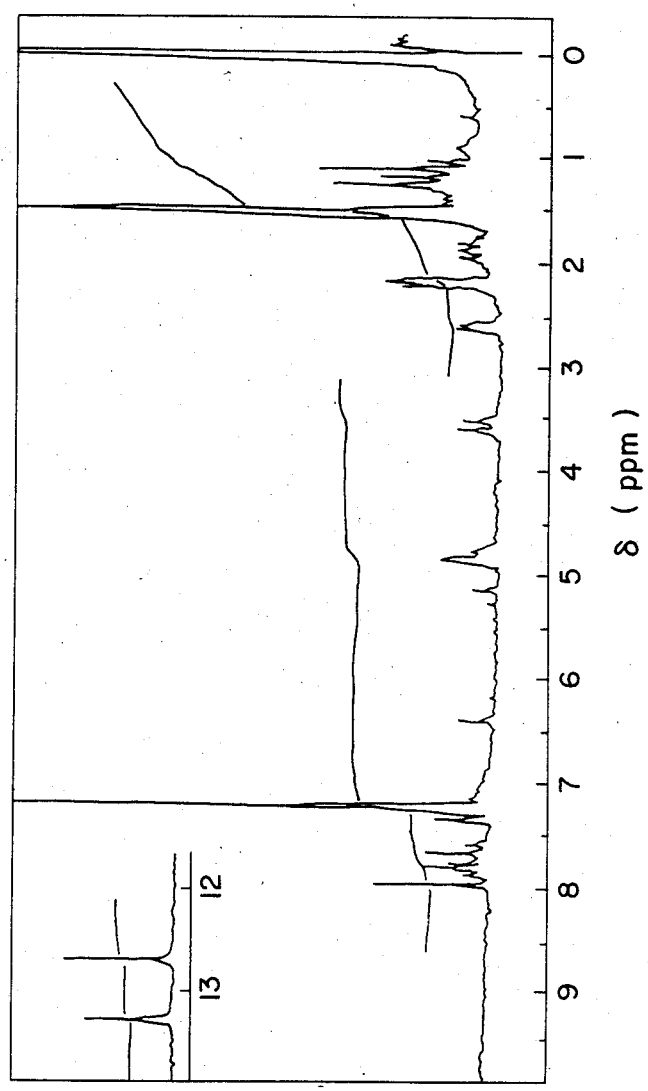
FIG. 1 is the nuclear magnetic resonance spectrum of the aglycone of serirubicin.
Figure 2:
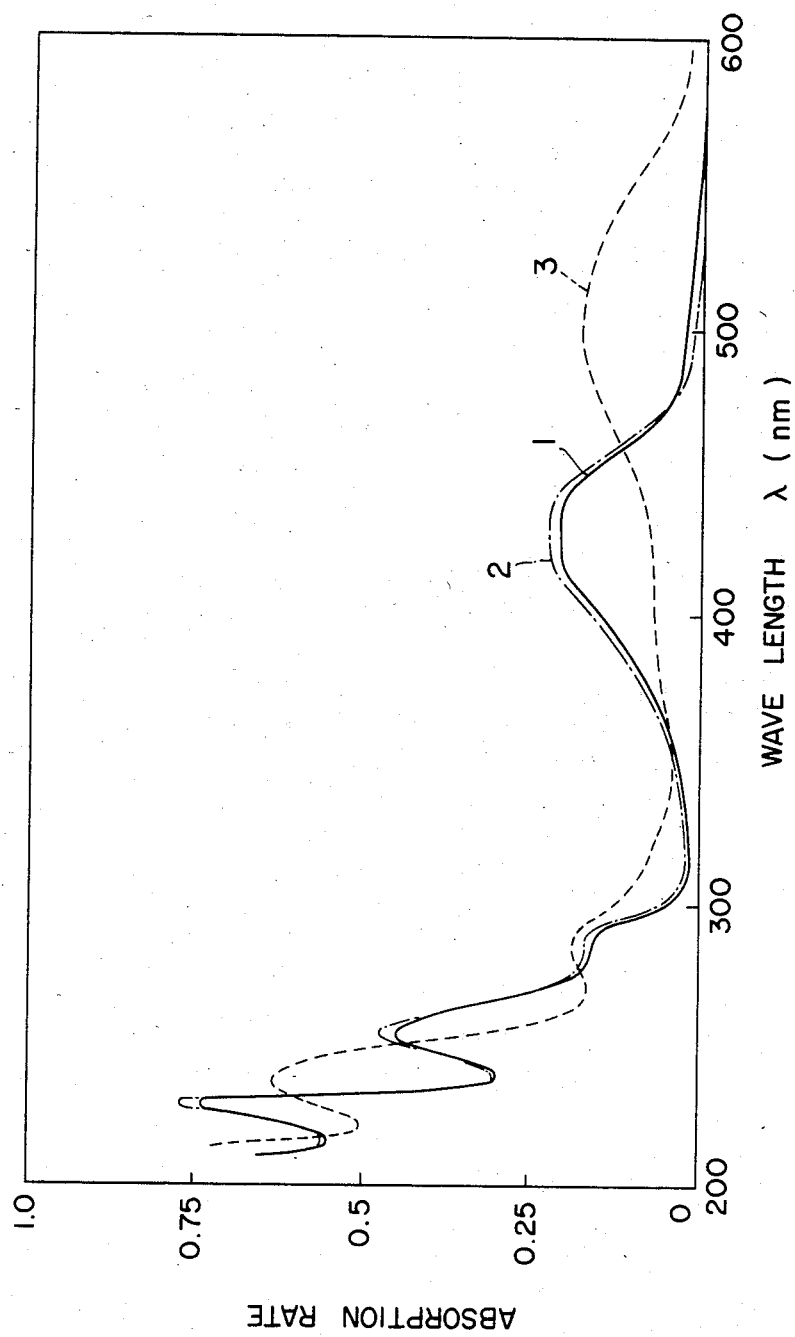
FIG. 2 is the ultraviolet/visible absorption spectrum of the aglycone of serirubicin in methanol (concentration in methanol; 10 $\mu$ g/ml)

Serirubicin was dissolved in 0.1N hydrochloric acid, heated for 30 minutes at 85° C. for hydrolysis, and extracted with chloroform to obtain a yellow aglycone. The Rf value on a silica gel plate, mass spectrum (m/z 370 (M+)), nuclear magnetic resonance spectrum (FIG. 1), ultraviolet/visible absorption spectrum (FIG. 2), and melting point (135+2° C.) identified the resulting aglycone as α-citromycinone of the following formula (2), a substance reported by Hans Brockmann et al. (Chemische Berichte, 101, pp. 1341–1348, 1968).

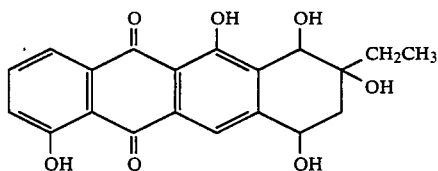

(2)

The water-soluble portion after hydrolysis was neutralized with silver carbonate, and developed with an n-butanol:acetic acid:water (4:1:1) solvent mixture on a silica gel plate to examine its saccharidal composition. The constituent saccharides were identified by spraying p-anisaldehyde-sulfuric acid over the silica gel plate after development, heating the plate for about 5 minutes at 80° C., and judging the colors of the colored spots and comparing the Rf values of the spots with those of standard samples. The saccharides constituting serirubicin were rhodosamine, 2-deoxyfucose and cinerulose B, all contained in equimolar amounts.

Then, serirubicin was catalytically reduced for 30 minutes at room temperature and atmospheric pressure with 5% Pd/BaSO$_4$ as a catalyst, whereby a trisaccharide composed of cinerulose B, 2-deoxyfucose and rhodosamine was released. A fresh yellow glycoside obtained by this reaction was purified by using a silica gel plate.

On FD-mass spectrographic analysis, this glycoside gave a peak at m/z 752 (M$^+$+1). Hydrolysis of the glycoside in the presence of hydrochloric acid formed γ-citromycinone (Chemische Berichte, 101, pp. 1341–1348, 1968), rhodosamine, 2-deoxyfucose and cinerulose B. The glycoside was thus found to be an anthracycline glycoside as expressed by the following formula (3):

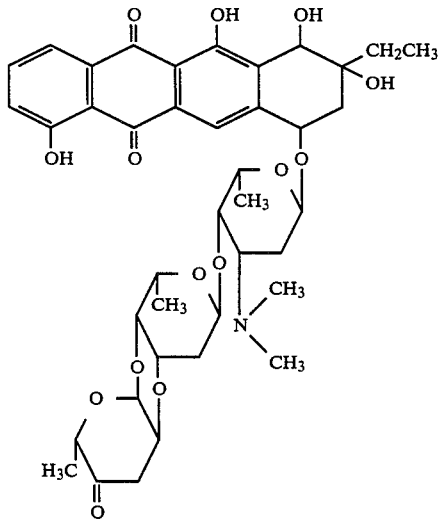

(3)

Figure 4:
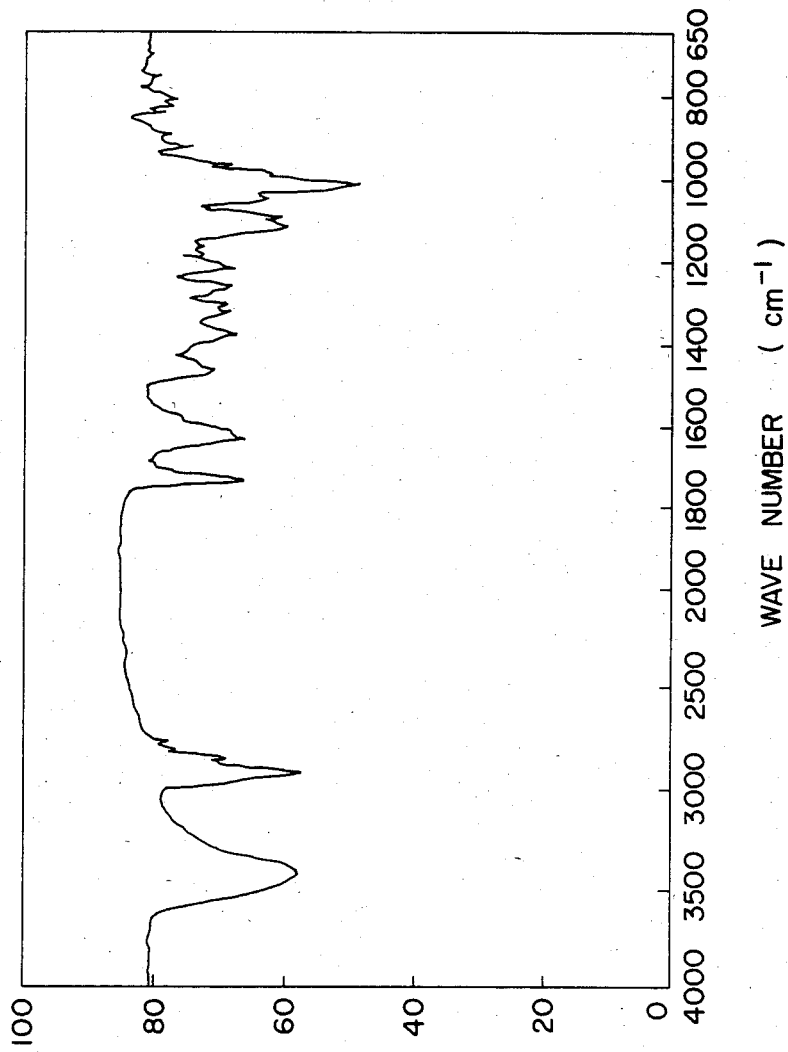
FIG. 4 is the infrared absorption spectrum of serirubicin tableted in potassium bromide.
Figure 5:
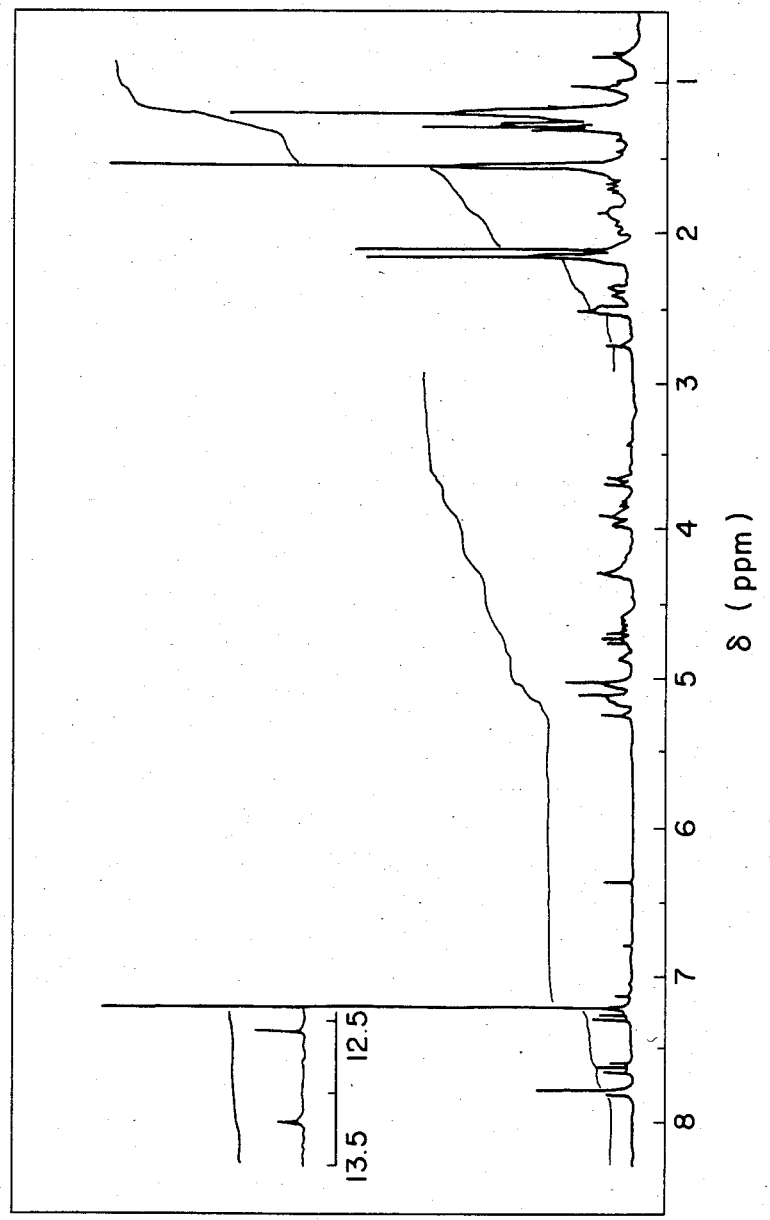
FIG. 5 is the nuclear magnetic resonance spectrum of serirubicin (250 MHz, in deuterochloroform).

From the above results, the infrared absorption spectrum (FIG. 4), and NMR spectrum (FIG. 5) of the chemical of the present invention, and its FD-mass spectrum with a peak at m/z 1165 (M$^+$+1), it was determined that serirubicin has a structure of the formula (1).

(3) Physicochemical properties of serirubicin
(a) Appearance: Yellow powder
(b) Elemental analysis (%):

Found: C 60.71, H 7.15; N 2.40, O 29.74;
Calcd: (for C$_{60}$H$_{82}$N$_2$O$_{21}$) C 61.84, H 6.92; N 2.40, O 28.83;
(c) Molecular weight: 1165.29
(d) Melting point: 165°–169° C.
(e) Specific rotatory power:

$[\alpha]_D^{25} = -52 \pm 3°$ (C:0.1 in CHCL$_3$)

Figure 3:
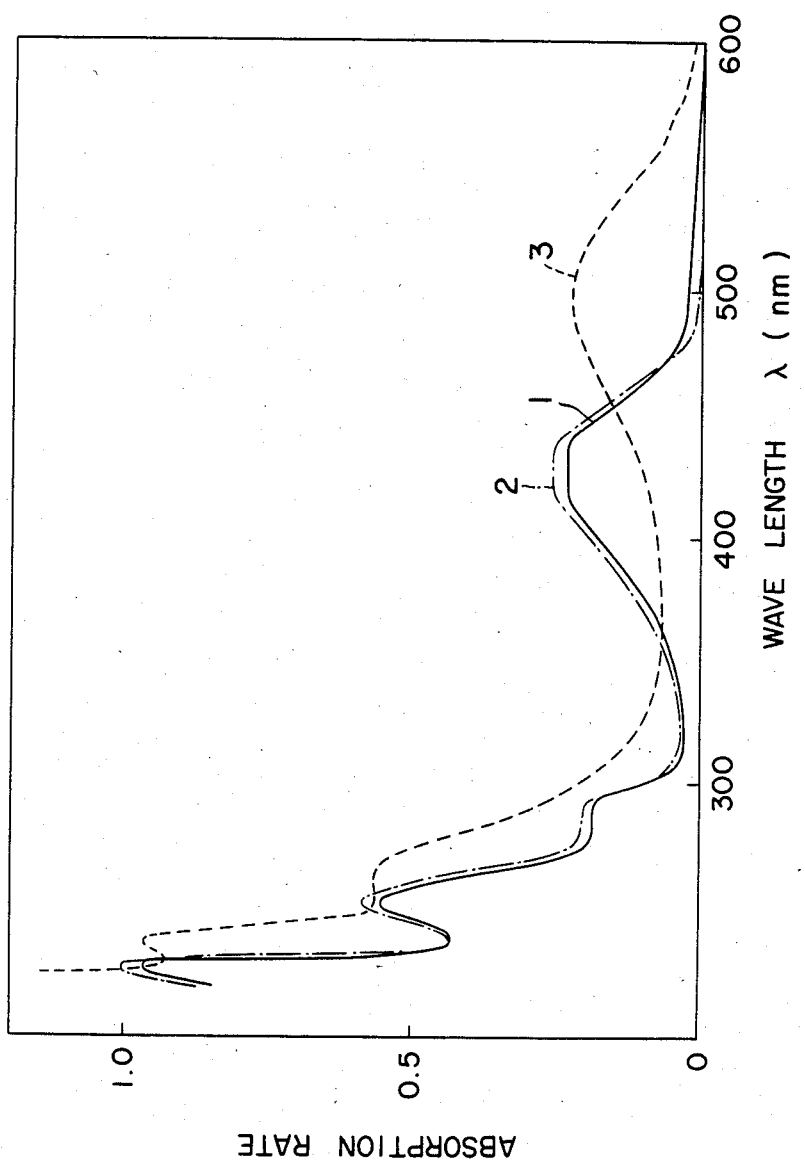
FIG. 3 is the ultraviolet/visible absorption spectrum of serirubicin in methanol (concentration in methanol: 30 $\mu$g/ml)

(f) Ultraviolet and visible absorption spectrum in methanol:
Shown in FIG. 3. Details are given in Table 1.

TABLE 1

| Solvent | $\lambda$max (E$_1^{\%}$$_{cm}$) |
| --- | --- |
| Methanol (Curve 1) | 229(262), 255(150), 293(52) 420(65), 438(65) |
| 0.1 N hydrochloric acid 90% methanol (Curve 2) | 229(295), 255(177), 292(62) 420(77), 438(77) |
| 0.1 N sodium hydroxide 90% methanol (Curve 3) | 239(264), 267(153), 500(63) |

(g) Infrared absorption spectrum (KBr tablet): Shown in FIG. 4.
(h) Nuclear magnetic resonance spectrum (250 MHz, in deuterochloroform): Shown in FIG. 5.
(i) Solubility: Serirubicin is soluble in methanol, acetone, ethyl acetate, chloroform, acetonitrile, and dimethyl sulfoxide (DMSO), and sparingly soluble in water, n-hexane and petroleum ether. Serirubicin is yellow in methanol, but turns reddish purple in the alkaline condition.
(j) Others: Serirubicin produces a negative ninhydrin reaction, and does not reduce Fehling's solution. On silica gel plate using various solvent systems, serirubicin has the Rf values shown in Table 2.

TABLE 2

| Developer | Rf Value |
| --- | --- |
| Chloroform:methanol (20:1) | 0.80 |
| Chloroform:methanol:acetic acid (20:2:0.1) | 0.72 |
| Ethyl acetate:methanol (10:1) | 0.27 |

2. Production of serirubicin (1) Outline

The anthracycline compound, serirubicin, can currently be obtained only by the cultivation of microorganisms. It may be possible, however, to produce this compound by the synthetic chemical or microbiological modification of analogous compounds, or to produce it by total chemical techniques. The cultivation technique uses strains of Streptomyces which have the ability to produce the anthracycline compound, serirubicin. More specifically, we have isolated a strain called Streptomyces cyaneus MG344-hF49, which produces serirubicin. Other suitable strains which produce serirubicin can be isolated from the natural environment by customary methods for use in the isolation of antibiotics-producing micro-organisms. It may be also possible to increase the serirubicin output by subjecting serirubicin-producing microorganisms (including S. cyaneus MG344-hF49) to radiation treatment or other treatments.

(2) MG344-hF49

MG344-hF49, a serirubicin-producing strain of Streptomyces discovered by us, will be described in detail below.

(1) Origin and Deposit No.

S. cyaneus MG344-hF49 is an actinomyces isolated from the soil within the site of the Institute of Microbial Chemistry in August 1980. This strain was deposited on June 28, 1982 with the Fermentation Research Institute, Agency of Industrial Science and Technology, Ministry of International Trade and Industry of Japan, where it was assigned the accession number FERM-P No.6605, which strain now bears the accession number FERM BP-314 under the Budapest Treaty on the International Recognition of the Deposit of Microorganism for the Purposes of the Patent Procedure.

(2) Microbiological characteristics

A. Morphology

Microscopically, substrate mycelia of MG344-hF49 are branched and extended aerial hyphae. On the aerial hyphae, hooks or spirals are formed, but no whirls are observed. Chains of mature spores include those having more than 10 spores. The spores range in size from about 0.4 to 0.6×0.8 to 1.0 micron, and their surfaces are spiny.

B. Culture characteristics on various media

In the following disclosure, the standards indicated in square brackets [] to describe colors comply with the Color Harmony Manual issued by the Container Corporation of America.

(a) On sucrose nitrate agar medium (cultured at 27° C.:

Growth is dull reddish purple [9 le, Raspberry], and white aerial mycelium develops slightly; purple soluble pigment is produced.

(b) On glucose-asparagine agar medium (cultured at 27° C.):

Growth is yellowish red [6 la, Lt Coral Red - 6 pc, Paprika], and on the growth light bluish gray [18 ec, Lt Aqua] aerial mycelium develops; reddish soluble pigment is produced.

(c) On glycerol-asparagine agar medium (ISP-5, cultured at 27° C.):

Growth is grayish purple [9 lg, Rose Plumn], and on the growth white to grayish white to light bluish gray aerial mycelium develops; no soluble pigment is produced.

(d) On starch-inorganic salts agar medium (ISP-4, cultured at 27° C.):

Growth is pale pink, and on the growth white to grayish bluish green [19 ie, Turquoise Green] aerial mycelium develops; pinkish soluble pigment is produced.

(e) On tyrosine agar medium (ISP-7, cultured at 27° C.):

Growth is light brown to dark brown, and grayish white to light bluish gray aerial mycelium develops on the growth; slightly brownish soluble pigment is produced.

(f) On nutrient agar medium (cultured at 27° C.):

Growth is grayish reddish purple [8 le, Rose Wine], and bright purplish gray aerial mycelium develops on the growth; brown soluble pigment is produced.

(g) On yeast extract-malt extract agar medium (ISP-2, cultured at 27° C.):

Growth is grayish reddish purple [9 ne, Raspberry], and white to purplish white to bluish white aerial mycelium develops on the growth; no soluble pigment is produced.

(h) On oatmeal agar medium (ISP-3, cultured at 27° C.):

Growth is pale pink to dull purple [10 pc, Fuchsia Purple], and light bluish gray to grayish bluish green [21 li, Dk Jade Gray] aerial mycelium develops on the growth; reddish soluble pigment is produced.

(i) Glycerol-nitrate agar medium (cultured at 27° C.):

Growth is grayish purple [9 le, Raspberry], and white aerial mycelium develops slightly on the growth; purple soluble pigment is produced.

(j) Starch agar medium (cultured at 27° C.):

Growth is dull grayish reddish purple [7½ le, Rose Wine], and no aerial mycelium develops; purple soluble pigment is produced.

(k) On calcium malate agar medium (cultured at 27° C.):

Growth is pale purple, and white aerial mycelium develops slightly on the growth; purplish soluble pigment is produced.

(l) On cellulose medium (filter paper-containing synthetic liquid, cultured at 27° C.):

No growth is observed.

(m) On gelatin stab culture medium:

On simple gelatin medium (cultured at 20° C.), growth is pale yellow, white aerial mycelium slightly develops on the growth, and brown soluble pigment is produced. On glucose peptone gelatin medium (cultured at 27° C.), growth is colorless to pale yellow, pinkish white aerial mycelium develops on the growth, and dark brown soluble pigment is produced.

(n) On skimmed milk medium (cultured at 37° C.):

Growth is pink to grayish red, and white aerial mycelium develops slightly on the growth; brownish soluble pigment is produced.

(3) Physiological properties

A. Properties (a) Growth temperatures:

Tests for growth were carried out at temperatures of 20°, 24°, 27°, 30°, 37° and 50° C. on glucose-asparagine agar medium. Growth occurred at all these temperatures, except at 50° C., and the optimum temperature is considered to be about 30° to 37° C.

(b) Liquefaction of gelatin (15% simple gelatin: cultured at 20° C.; glucose peptone gelatin: cultured at 27° C.):

On simple gelatin medium, liquefaction began after 5 days of cultivation. On glucose peptone gelatin medium, liquefaction was not observed after 2 weeks of cultivation, and slight liquefaction was seen after 3 weeks. The liquefactive strength is considered to be normal to poor for simple gelatin, and poor for glucose peptone gelatin.

(c) Hydrolysis of starch (tested on starch-inorganic salts agar medium, and starch agar medium, each cultured at 27° C.):

Hydrolysis was observed after 3 days of cultivation. The hydrolytic strength is normal to poor.

(d) Coagulation and peptonization of skimmed milk (cultured at 37° C.):

Coagulation began after 3 days of cultivation, and was completed after 7 days, when peptonization began. The strength is normal.

(e) Production of melanoid pigment (tested on tryptone-yeast extract broth (ISP-1), peptone-yeast extract iron agar medium (ISP-6) and tyrosine agar medium (ISP-7), each cultured at 27° C.):

Melanoid pigment was produced in all these media.

(f) Utilization of carbon sources (tested on Pridham-Gottlieb agar medium (ISP-9) at 27° C.):

L-arabinose, D-xylose, D-glucose, D-fructose, sucrose, inositol, L-rhamnose, raffinose, and D-mannitol were all utilizable for growth.

(g) Dissolution of calcium malate (tested on calcium malate agar medium cultured at 27° C.):

Calcium malate was dissolved around the periphery of growth after 7 days of cultivation, but this dissolving action was weak.

(h) Nitrate reduction (tested on 1.0% potassium nitrate-containing peptone water (ISP-8) cultured at 27° C.):

Reduction was positive.

B. Conclusion and identification as a new strain

The characteristics described above can be summarized as follows:

The strain MG344-hF49 belongs to Streptomyces, and the cell wall contains 2,6-diaminopimelic acid of the LL-type. No sporangium is observed, spirals are formed on aerial hyphae, and no whirls are seen. The surface of spores is spiny. Growth on various media is pale pink to grayish reddish purple or yellowish red, and white to bright bluish gray to grayish bluish green aerial mycelium develops on the growth. Purple or reddish soluble pigment is produced. The back of the growth provides a pH indicator, changing from purple to bluish purple or blue on addition of 1N NaOH. Melanoid pigment production is positive, and proteolytic activity is medium to weak. Degree of hydrolysis of starch is also medium to weak.

If these characters are compared with those of known species, the strain MG344-hF49 is closest to Streptomyces cyaneus [International Journal of Systematic Bacteriology, Vol. 22, page 290, 1972 (Reference 1); Waksman's The Actinomycetes, Vol. 2, page 199, 1961 (Reference 2); Bergey's Manual of Determinative Bacteriology, 7th Ed., page 757, 1957 and 8th Ed., page 822, 1974 (Reference 3)]. The properties of the strain MG344-hF49 and Streptomyces cyaneus described in the literature will be compared below.

TABLE 3

| | MG344-hF49 | Streptomyces cyaneus ISP 5108 |
|---|---|---|
| Shape of aerial hypha | Spiral | Spiral |
| Surface of spore | Spiny | Spiny |
| Color of aerial mycelium | White to bright bluish gray to grayish bluish green | Pale blue to bluish gray |
| Color of growth | Pale pink to grayish reddish purple | Dark grayish blue to dark grayish purple |
| Soluble pigment | to purplish, or sometimes reddish | to purplish or bluish |
| Production of melanoid pigment | + | + |
| Hydrolysis of starch | + medium to weak | + weak* |
| Coagulation of milk | + | +* |
| Peptonization of milk | + | +* |
| Liquefaction of gelatin | + medium to weak | + strong* |
| Reduction of nitrate | + | −* |
| Utilization of carbon sources: | | |
| D-glucose | + | + |
| L-arabinose | + | + |
| D-xylose | + | + |
| D-fructose | + | + |
| Sucrose | + | + |
| Inositol | + | + |
| L-rhamnose | + | + |
| Raffinose | + | + |
| D-mannitol | + | + |
| pH indicator | + | + |

*Disclosed in References 2 and 3 cited earlier.

As shown in Table 3, the strain MG344-hF49 and Streptomyces cyaneus have practically the same properties, except for the reduction of nitrate. The property of reducing nitrates is minimally stable in the case of actinomyces, and it is difficult to distinguish between MG344-hF49 and Streptomyces cyaneus on the basis of the difference in the nitrate-reducing property.

Accordingly, MG344-hF49 was considered to be very close to Streptomyces cyaneus. Thus, we identified MG344-hF49 as Streptomyces cyaneus MG344-hF49.

(3) Cultivation for production of serirubicin

The anthracycline compound, serirubicin, can be produced by cultivating a serirubicin-producing strain of Streptomyces aerobically in a suitable medium, and recovering the object product from the cultured medium.

Culture media may be those containing any nutritional sources which can be utilized by serirubicin-producing microorganisms. For example, glycerol, glucose, sucrose, maltose, dextrin, starch and fats are useful as carbon sources. Examples of nitrogen sources are organic materials such as soybean flour, cotton seed meal, meat extract, peptone, dry yeast, yeast extract and corn steep liquor, and inorganic materials such as ammonium salts or nitrates (e.g., ammonium sulfate, sodium nitrate and ammonium chloride). If desired, inorganic salts such as sodium chloride, potassium chloride, phosphates, and salts of heavy metals can also be added. In order to prevent foaming during fermentation, suitable anti-foaming agents such as silicone may be added by customary methods. The most suitable method of cultivation is aerobic deep liquid culture which is employed widely for the production output of antibiotics. The suitable cultivation temperature is 20° to 35° C., preferably 25° to 30° C. With this method, the production of serirubicin reaches its maximum after 3 to 7 days of shake culture, or culture under aeration and stirring.

There can thus be obtained cultured broths in which serirubicin is accumulated. In the resulting cultured broth a part of the accumulated serirubicin is present in the bacterial cells, but most parts thereof is present in the filtrate of the cultured broth.

Serirubicin can be recovered from such cultured broths by any methods suitable for the recovery. One of the methods is based on extraction. For example, serirubicin in the filtrate of the cultured broth can be recovered by extraction with a water-immiscible solvent for serirubicin (see the foregoing description in the specification), such as ethyl acetate, butyl acetate, chloroform or butanol (a good efficiency of extraction being obtained when the cultured broth filtrate is neutral or weakly basic). Serirubicin in the bacterial cells can be recovered by treating the bacterial cells, which have been collected by filtration or centrifugation, with ethyl acetate, chloroform, methanol, ethanol, butanol, acetone, methyl ethyl ketone, a hydrochloric acid solution, or an acetic acid solution. It is also possible to subject the cultured broth as such to the abovementioned extraction step without preliminarily isolating the bacterial cells. The bacterial cells that may be crushed and then extracted. Counter-current distribution may be included in the extraction methods. Another technique for recovering serirubicin from the cultured broth is based on adsorption. A serirubicin-containing liquid material, such as cultured broth filtrate, or the extract obtained by the aforementioned extraction procedure, is subjected to column chromatography, liquid chromatography or the like using a suitable adsorbent, such as activated carbon, alumina, silica gel or Sephadex LH20 (a product of Pharmacia AB). The adsorbent having the object product, serirubicin, adsorbed onto it is eluted to give serirubicin. The resulting serirubicin solution is concentrated to dryness under reduced pressure to obtain a crude form of serirubicin as a red powder.

The crude serirubicin can be purified by performing the aforementioned extraction and adsorption techniques (if desired, in combination) over a desired number of times, followed by recrystallization, if desired. For example, purification can be done by combinations of column chromatography using adsorbents or gel filter such as silica gel, Sephadex LH-20, a weakly acidic ion exchange resin, or Diaion HP-20 (a product of Mitsubishi Chemical Industries, Ltd.); liquid chromatography using a suitable solvent; counter-current distribution; and thin-layer chromatography. A concrete example of the purification method comprises dissolving a crude powder of serirubicin in a small amount of chloroform, applying the solution to a silica gel column, and developing the column with a suitable solvent to elute the respective active ingredients in the separate condition. The desired active fractions are combined and concentrated under reduced pressure. The residue is subjected to thin-layer chromatography, and the desired component is scraped off, thereby obtaining a product consisting substantially of a single component. Further purification can be achieved by high-performance liquid chromatography, or crystallization from a suitable solvent.

3. Uses of serirubicin

The anthracycline compound, serirubicin, in accordance with the present invention has carcinostatic activity and antimicrobial activity, and thus, it is useful as a medicine.

(1) Physiological activities (1) Antitumor activity $CDF_1$ mice were intraperitoneally implanted with $1 \times 10^5$ L1210 leukemia cells/mouse as a suspension. After the implantation, 0.25 ml of a solution containing the test compound was intraperitoneally injected into each mouse, each day, for 10 days, beginning on the day of implantation. The mice were observed for 30 days, and the number of days during which the mice survived (hereinafter referred to as survival days) was counted.

The increase of life span (%) compared with the control group consisting of mice administered with physiological saline solution instead of the test compound solution was calculated from the following equation:

$$\frac{\text{Number of survival days for the test compound group}}{\text{Number of survival days for the control group}} \times 100 \, (\%)$$

The results are shown in Table 4.

TABLE 4

| Dose (mg/kg/day) | Increase of life span (%) |
|---|---|
| 1.0 | 149 (toxic tendency) |
| 0.5 | 143 |
| 0.25 | 274 |
| 0.125 | 137 |
| 0.063 | 113 |
| 0.031 | 119 |

(2) Acute toxicity ($LD_{50}$)

$LD_{50}$ of serirubicin according to the present invention after a single intraperitoneal infection in mice was 10 to 20 mg/kg.

(3) Action on cultured cancer cells

Serirubicin according to the present invention inhibited the growth of cultured L1210 cells at very low concentrations. This compound also inhibited the synthesis of various polymers; RNA synthesis was inhibited at particularly low concentration. These findings indicated its therapeutic effect on tumors in experimental animals.

TABLE 5

| L1210 cells | $ID_{50}$ (μg/ml) |
|---|---|
| Growth | 0.004 |
| DNA synthesis | 0.46 |
| RNA synthesis | 0.086 |
| Protein synthesis | inhibition of 32% at 10 μg/ml |

(4) Antimicrobial activity

The antimicrobial activity of serirubicin according to the present invention was examined. It is expressed as minimum inhibitory concentration (MIC) determined by the agar dilution method. The results are tabulated below.

TABLE 6

| Microorganism | MIC (μg/ml) |
|---|---|
| S. aureus 209P | 0.78 |
| S. aureus Smith | 1.56 |
| S. aureus MS8710 | 0.78 |
| S. aureus MS9610 | 0.78 |
| M. lysodeikticus IF03333 | 0.78 |
| B. subtilis PCI219 | 0.78 |
| B. cereus ATCC10702 | 0.78 |
| Coryn. bovis 1810 | 0.39 |
| E. coli NIHJ | >3.12 |
| K. pneumoniae PCI 602 | >3.12 |
| Sal. typhi T-63 | >3.12 |
| Serr. marcessens | >3.12 |
| Prot. vulgaris OX 19 | >3.12 |
| Pseu. aeruginosa A3 | >3.12 |

(2) Antitumor agents

As described above, the anthracycline compound, serirubicin, according to the present invention was demonstrated to have antitumor activity against tumors, particularly, malignant tumors, in animals.

Accordingly, serirubicin of this invention or its acid addition salts can be used as pharmaceutical compositions to control or treat tumors.

Serirubicin or its acid addition salts as antitumor agents can be administered by any route suited to the intended objects in dosage forms determined by the route of administration. Usually, serirubicin or its acid addition salts diluted with pharmaceutically acceptable carriers or diluents are administered as drugs.

For example, serirubicin or its acid addition salts of the present invention can be administered singly or as mixtures with a carrier such as maltose or lactose or as non-toxic complexes, such as complexes with deoxyribonucleic acid. The deoxyribonucleic acid may be that extracted from cells of animals or microorganisms, such as calf's thymus, HeLa cells or yeast.

A typical method of administering serirubicin or its acid addition salts of the present invention is by injection of a solution thereof in distilled water for injection use or in physiological saline. Examples of injection include intraperitoneal injection, subcutaneous injection, intravenous or intraarterial injection, and local injection in animals; and intravenous or intraarterial injection, and local injection in man. The dose is determined with consideration of the results of animal experiments and varying circumstances in such a manner that a total of doses given continuously or intermittently will not exceed a predetermined limit. It goes without saying that specific doses should be varied depending on the mode of administration, and situations of animal subjects, such as age, body weight, sex, susceptibility, food, times of administration, concomitant drugs, condition of animals or the severity of their deseases. The optimal doses and the frequency of administration under certain conditions must be determined by experts' optimum dose determination studies on the basis of the above-mentioned factors.

(3) Pharmaceutical compositions for treatment of gram-positive bacterial infections As the physiological activity data have demonstrated, serirubicin of this invention is a carcinostatic antibiotic. Specifically, serirubicin or its acid-addition salts exhibit antimicrobial activity against gram-positive bacteria, and thus, can be used as antibiotics effective against staphylococcal infections, diphtheria, pneumonia, etc. The suitable dosage forms and doses can be determined as already explained hereinabove in regard to the use as antitumor agents. The frequency of administration, etc. can be determined with the same care as described previously.

4. Experimental Examples

Example 1

(1) Inoculum preparation

A medium used to grow the primary inoculum was prepared according to the following recipe:

| | |
|---|---|
| Galactose | 2% |
| Dextrin | 2% |
| Bacto soytone (a trade name) | 1% |
| Corn steep liquor | 0.5% |
| Calcium carbonate | 0.1% |
| pH before sterilization | 7.4 |

A loopful of spores from a slant culture of Streptomyces cyaneus MG344-hF49 was used to inoculate each of 500 ml. Erlenmeyer flasks each containing 100 ml of the above medium, which had been sterilized. The flasks were placed on a rotary shaker, and the inoculated medium was shake-cultured for 72 hours at 27° C. to prepare an inoculum.

(2) Cultivation

A Fermentation medium was prepared according to the following recipe:

| | |
|---|---|
| Dextrose | 3% |
| Glucose | 0.3% |
| Toast Soya (a trade name for soy bean flour) | 2% |
| Cobalt chloride | 0.12 g/l |
| Calcium carbonate | 0.3% |

500 ml of inoculum, prepared as described in the step (1), was added to a 30 liter jar fermentor containing 15 liters of the above fermentation medium that had been sterilized. The fermentation was carried out for 90 hours at a temperature of 27° C. at an aeration rate of 15 liters per minute and an agitation speed of 150 r.p.m.

(3) Isolation of serirubicin

The fermented mash from the step (2) was filtered, and the filtrate was adjusted to a pH of 8.0, which step was followed by extraction with 10 liters of butyl acetate. The supernatant of the extract was concentrated to obtain 20 g of an oily material. The oily material was dissolved in a small amount of chloroform, and the solution was adsorbed onto a 100 g silica gel (Kiesel Gel 60, product of E. Merck) column. A stepwise elution of the column was carried out using chloroform-methanol with varying mixing proportions. Fractions containing serirubicin were collected and concentrated to obtain 175 mg of serirubicin as a red crude powder.

Example 2

100 mg of the red crude powder obtained in Example 1 was dissolved in a small amount of chloroform. The solution was adsorbed onto ten 20×20 cm thin layers (thickness: 0.25 mm) of silica gel (Kiesel Gel 60 $F_{254}$, a product of Merck). The thin layers were developed with a 100:5:0.02 mixture of chloroform, methanol and concentrated ammonium hydroxide. The separated serirubicin-containing regions were scraped off and eluted with chloroform-methanol (10:1). The so obtained fraction was concentrated, and the residue was chromatographed on a 1.0×20 cm column of Sephadex LH-20 that had been equilibrated chloroform-methanol (1:1). The column was developed with chloroformmethanol (1:1). The active fraction was dried under reduced pressure to obtain 1.5 mg of serirubicin as a yellow powder. This product was further purified by high-performance chromatography using Water's unit under the following conditions:

Column: Two components (Censho Pack $N_5C_{18}$ and ERC Pack ODS-1172) connected together in series Solvent: Acetonitrile: 0.3M ammonium formate buffer (pH 2.5)=20:1
Flow rate: 6 ml/min.
Serirubicin was eluted in 9.2 minutes. The eluate gave 1.1 mg of serirubicin as a single-component substance.
What is claimed is:
1. An anthracycline compound, serirubicin, of the formula (1):
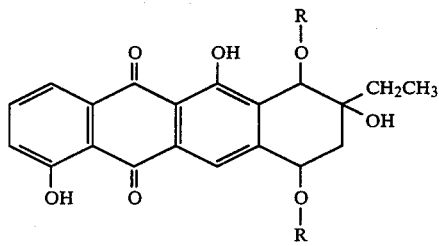
(1)
wherein R represents the substituent:
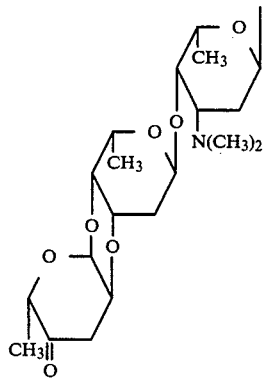
or an acid addition salt of the serirubicin.
* * * * *